US006136858A

United States Patent [19]
Kuchan et al.

[11] Patent Number: 6,136,858
[45] Date of Patent: *Oct. 24, 2000

[54] INFANT FORMULA AND METHODS OF IMPROVING INFANT STOOL PATTERNS

[75] Inventors: Matthew A. Kuchan, Gahanna; Marc L. Masor, Worthington, both of Ohio; Debra L. Ponder, Atlanta, Ga.; Robin J. Halter, Columbus, Ohio; John D. Benson, Powell, Ohio; Gary E. Katz, Columbus, Ohio

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/812,626

[22] Filed: Mar. 7, 1997

Related U.S. Application Data

[63] Continuation-in-part of application No. 08/585,221, Jan. 11, 1996, Pat. No. 5,700,590, which is a continuation-in-part of application No. 08/178,687, Jan. 10, 1994, Pat. No. 5,492,899.

[51] Int. Cl.[7] .............................. A61K 31/20; A23D 9/00
[52] U.S. Cl. ..................... 514/560; 424/489; 514/558; 514/866; 426/801; 426/601; 426/656; 426/658; 426/607
[58] Field of Search ........................... 424/489; 514/558, 514/560, 866; 426/801, 601, 656, 658, 607

[56] References Cited

U.S. PATENT DOCUMENTS

| | | | |
|---|---|---|---|
| 3,231,385 | 1/1966 | Ziro et al. | 426/72 |
| 3,649,295 | 3/1972 | Bernhart | 426/598 |
| 4,544,559 | 10/1985 | Gil | 426/72 |
| 4,670,285 | 6/1987 | Clandinin et al. | 426/602 |
| 4,758,553 | 7/1988 | Ogashi | 514/47 |
| 4,994,442 | 2/1991 | Gil et al. | 514/45 |
| 5,000,975 | 3/1991 | Tomarelli | 426/602 |
| 5,021,245 | 6/1991 | Borschel et al. | 426/2 |
| 5,066,500 | 11/1991 | Gil et al. | 426/72 |
| 5,075,225 | 12/1991 | Wong | 435/87 |
| 5,221,545 | 6/1993 | Borschel et al. | 426/2 |
| 5,223,285 | 6/1993 | DeMichele et al. | 426/72 |
| 5,234,702 | 8/1993 | Katz et al. | 426/72 |
| 5,268,365 | 12/1993 | Rudolph et al. | 514/44 |
| 5,488,039 | 1/1996 | Masor et al. | 514/43 |
| 5,492,899 | 2/1996 | Masor et al. | 514/47 |
| 5,602,109 | 2/1997 | Masor et al. | 514/45 |
| 5,700,590 | 12/1997 | Masor et al. | 426/656 |
| 5,922,766 | 7/1999 | Acosta et al. | 514/561 |

FOREIGN PATENT DOCUMENTS

| | | |
|---|---|---|
| 1709692 | 7/1992 | Australia . |
| 0129990 | 6/1984 | European Pat. Off. . |
| 302807 | 5/1988 | European Pat. Off. . |
| 375408 | 12/1989 | European Pat. Off. . |
| 0376628 | 12/1989 | European Pat. Off. . |
| 2152814 | 12/1984 | United Kingdom . |
| 2216416 | 3/1989 | United Kingdom . |

OTHER PUBLICATIONS

L.M. Janas, et al., "The Nucleotide Profile of Human Milk" Pediatric Research, vol. 16, pp. 659–662, 1992.

A. Gil, et al., "Acid–Soluble Nucleotides of Human Milk at Different States of Lactation", J. of Dairy Research, vol. 49, pp. 301–307, 1992.

J. Leach, et al., "Nucleic Acid Content of Enteral Formulas" Fed. Soc. Exp. Biology, Abstract #2184, p. A378, Mar., 1993.

J. Espinoza, et al., "Nucleotide Enriched Milk and Diarrheal Disease in Infants," Mar., 1993, Federation Society Experimental Biology, Abstract #16, p. 739.

L. Zhang, et al., "Immunomodulatory actions of nucleotides on Ag/Ig production . . . ", Fed. Soc. Exp. Biology, Abstract #2389, Mar., 1993.

O'Brunser, et al., "Effect of Dietary Nucleotide Supplementation on Diarrhoel Disease in Infants," Acta Pediatrics, vol. 83, pp. 188–191, 1994.

F.B. Rudolph, et al., "Role of RNA as a Dietary Source of Pyrimidines & Purines in Immune Function," Nutrition, vol. 6, pp. 45–52, 1990.

F.B. Rudolph, "Nucleotides: Micronutrient Building Blocks of Nutrition," Nutrition, Sep. 1989, pp. 8–13.

F. Oski, "The Evolution of Infant Formula," Nutrition, pp. 4–7, Sep., 1989.

L.A. Barness, "The Effects of Nucleotides on Aspects of Neonatal Immunity," Nutrition, pp. 20–24, 1989.

R.J. Chandra, "Nutrients and Immune Function," Nutrition, pp. 25–31, Sep., 1989.

J. Carver, et al., "Dietary Nucleotides May Act as Growth Factors in Liver and Intestine," Fed. Soc. Exp. Biology, Abstract #3726, p. A643, Mar., 1993.

Carver, et al., "Dietary Nucleotide Effects Upon Immune Function in Infants," Pediatrics, 88(2):359, 1991.

Berlitz, et al., "Lehrbuch der Lebensmittelchemie," Springer–Verlag. p. 392, 1985.

Leach, et al., "Total Potentially Available Nucleosides of Human Milk by Stage of Lactation," Amer. J. Clin. Nutrition, V. 61: No. 6, 1995.

A. K. Sedgwick, et al., "Rapid Quantitative Microenzyme–Linked Immunosorbent Assay for Tetanus Antibodies," J. Clin. Microbiology, Jul., 1983, vol. 18:104–109.

(List continued on next page.)

Primary Examiner—Francisco Prats
Attorney, Agent, or Firm—J. Michael Dixon; Thomas D. Brainard

[57] ABSTRACT

The invention is directed to an improved infant formula containing a lipid blend that softens the firmer stools associated with typical infant formula. A specific formula in accordance with the invention comprises carbohydrates, proteins, vitamins and minerals and a lipid mixture of high oleic safflower oil, soy oil and coconut oil at specific levels and ratios. The invention also discloses novel mixtures of fatty acids that provides infant stool patterns more closely resembling the breast-fed infant.

16 Claims, No Drawings

OTHER PUBLICATIONS

B. F. Anthony, et al., "Immunospecificity and Quantitation of an Enzyme–Linked Immunosorbent Assay for Group B Streptococcal Antibody," J. Clin. Microbiology, Aug., 1982, vol. 16:350–354.

D.M. Granoff, et al., "Antibody Responses to *Haemophilus influenzae* Type b Poly–saccharide Vaccine in Relation to Km(1) and G2m(23) Immunoglobulin Allotypes," J. Infectious Dis., Aug., 1986, vol. 154:257–264.

W.G. Wierda, et al., "Comparison of Fluorochrome–labeled and $^{51}$Cr–labeled targets for natural killer cytotoxicity assay," J. Immunol. Methods, 1989; 122:15–24.

B.W.C. Forsyth, et al., "Problems of early infancy, formula changes, and mothers' beliefs about their infants," J. Pediatr., 1985; 106:1012–1017.

L.T. Weaver, et al., "The Bowel Habit of Milk–Fed Infants," J. Pediatr. Gastroenterology and Nutr., 1988; 7:568–571.

J.S. Hyams, et al., "Effect of infant formula on Stool Characteristics of Young Infants," Pediatrics, 1995, 50–54.

S.J. Fomon, Nutrition of Normal Infants (L. Craven, ed.) Mosby: St. Louis, Missouri, p. 250, (1997).

P.T. Quinlan, et al., "The Relationship between Stool Hardness and Stool Composition in Breast– and Formula–Fed Infants," J. Pediatr. Gastroenterology and Nutr., 1995, vol. 20, No. 1, 81–90.

A. Gil, et al., "Changes In The Fatty Acid Profiles of Plasma Lipid Fractions Induced by Dietary Nucleotides in Infants Born at Term," Eur. J. of C. Nutrition, 1988; 42:473–481.

R. Halter, et al., "Stool Consistency Of Formula–Fed And Breast–Fed Infants," 1326, Experimental Biology 96, Apr. 14–17, 1996.

INFANT FORMULA AND METHODS OF IMPROVING INFANT STOOL PATTERNS

RELATED APPLICATIONS

This application is a continuation-in-part of U.S. patent application Ser. No. 08/585,221 filed Jan. 11, 1996; now U.S. Pat. No. 5,700,590 which is a continuation-in-part of U.S. patent application Ser. No. 08/178,687 filed Jan. 10, 1994 now U.S. Pat. No. 5,492,899 issued Feb. 20, 1996. The complete teachings of U.S. Pat. No. 5,492,899 are incorporated herein by reference.

FIELD OF THE INVENTION

The invention relates to an improved enteral nutritional formula and more particularly to infant formulas which contain a lipid fraction possessing a fatty acid profile resulting in more desirable infant stool patterns compared to stool patterns associated with conventional infant formula. More specifically, this invention relates to a blend of high oleic safflower oil, and/or high oleic sunflower oil, soy oil and coconut oil (or a blend of fats that have a similar fatty acid profile to the inventive blend) that has been found effective in producing stool patterns in infants that are similar to those of the breast-fed infant.

BACKGROUND OF THE INVENTION

The composition of human milk serves as a valuable reference for improving infant formula. However, human milk contains living cells, hormones, active enzymes, immunoglobulins and components with unique molecular structures that cannot be replicated in infant formula. Unlike human milk, infant formula must remain stable on the shelf for up to thirty-six (36) months. These fundamental differences between human milk and infant formula often mandate differences in the composition to achieve similar clinical outcome.

The study of human milk components has stimulated many investigations into what constituents may be added to an improved infant formula. Greater knowledge of the composition of human milk affords the opportunity to design infant formulas that are closer in composition to human milk. However, it becomes increasingly apparent that infant formula can never exactly duplicate human milk. Many constituents in human milk are bioactive and because of synergies among these components, there is little reason to believe that the same compound would have the same bioactivity in infant formula. The likelihood of this possibility is further diminished when the impact of heat treatment for sterilization and long-term storage of the formula is considered. The present invention is based, in part, on the concept of providing a formula which matches the performance of breast milk in stool consistency parameters without attempting to duplicate exactly the delicate balance of human milk components.

The composition of human milk differs appreciably from that of other species and much attention has been paid to the various components. Several investigators have reported on the nucleotide content of milk from humans (Janas, L M et al: The Nucleotide Profile of Human Milk. *Pediatr. Res.* 16:659–662(1982) and Gil et al.: Acid-soluble Nucleotides of Human Milk at Different Stages of Lactation. *Journal of Dairy Research* (1982), 49, 301–307). Numerous publications have also discussed various lipid, oil or fat blends for use in an artificial nutritional for human infants. As the result of investigations regarding the use of nucleotides in infant formula, the inventors of the present application discovered that a particular blend of oils resulted in infant stool patterns that are similar to those of the breast fed infant.

Formula tolerance is generally assessed by gastrointestinal symptoms (e.g., emesis, stool patterns and gas) as well as behavioral characteristics (e.g., acceptance of formula, fussing and crying). Concerns regarding poor tolerance are frequently reported as a reason for formula switching within the first two months of life. (Forsythe BWC, McCarthy P L, Leventhal J M: Problems of early infancy, formula changes, and mother's beliefs about their infants. *J. Pediatr.* 1985; 106:1012–1017). Stool patterns are known to differ between formula-fed and breast-fed infants, (Weaver L T, Ewing G. Taylor, L C: The Bowel Habit of Milk-Fed Infants. *J. Pediatr. Gastroenterol Nutr.* 1988; 7:568–571), as well as between infants fed various formulas (Hyams, J S, Treem W R, Etienne N L, et al.: Effect of infant formula on stool characteristics of young infants. *Pediatrics* 19951 50:54).

The Hyams et al. publication, supra, also reports that certain infant formulas typically cause a significantly greater percentage of firm stools compared to the breast-fed infant which may be perceived by the parent or care giver as unacceptable. This publication also indicated that milk-based, iron-fortified formulas resulted in a significantly lower percentage of watery stools. S. J. Fomon in *Nutrition of Normal Infants* (L. Craven ed.) Mosby: St. Louis, Mo., at page 250 states that "Many physicians appear to be convinced that infants fed iron-fortified formulas are prone to fussiness . . . and constipation." It is this problem and/or perception that the present invention addresses. Quinlan et al. in *Pediatr Gastroenteral Nutr.*, Vol. 20, No. 1 (1995) concludes that "Constipation" and "hard stools" are associated with formula feeding of both term and pre-term infants and, in the latter, can lead to life threatening complications."

Numerous investigators have reported that fatty acid profiles similar to human milk are important to the human infant. Representative of those numerous publications are: 1) Gil et al., changes in the Fatty acid Profiles of Plasma Lipid Fractions Induced by Dietary Nucleotides in Infants Born at Term, *Eur. J.* of C. Nutrition, (1988) 42, 473–481; 2) E.P. 0129,990; 3) E.P. 0376,628; 4) U.S. Pat. No. 4,670,285; 5) U.S. Pat. No. 3,231,385; 6) U.S. Pat. No. 4,544,559; 7) U.S. Pat. No. 4,758,553; and 8) U.S. Pat. No. 4,994,442. These investigators have failed to discover that a blend of lipid sources, which is essentially free of palmitic acid which may comprise a blend of high oleic safflower oil, soy oil and coconut oil, is beneficial in overcoming certain shortcomings associated with infant formula.

SUMMARY OF THE INVENTION

Previous investigations have attempted to duplicate the fatty acid profile of human milk in an effort to improve infant formula. In contrast, the present invention is based upon discovery that a particular fatty acid profile for the lipid not closely related to the profile of human milk, will result in a stool pattern similar to breast fed infant s while also supplying basic nutritional requirements. Such a lipid profile can be achieved, for example, through a blend of oils.

The enteral formula of the instant invention provides a positive advantage to the infant. The clinical studies which were conducted and reported herein evidence the unexpected advantages of the instant invention. An additional aspect of the present invention is the overall balance of nutrient interactions and bio-availability, which provide an improved nutritional product. Another aspect of the present invention relates to an infant formula which meets the requirements of the Infant Formula Act and to methods for reducing the incidence of objectionable stool characteristics associated with conventional infant formula. Further, the present invention is directed to a novel blend of oils which provide a fatty acid profile that is beneficial in human nutrition.

Thus, the invention provides, in one aspect an improved fat composition for consumption by humans characterized by a fatty acid profile comprising 9.5–21 weight % lauric acid, up to 10 weight % palmitic acid and 34–48 weight % oleic acid. In another aspect, the invention provides an enteral formula comprising protein, carbohydrate and a fat composition as described above.

Yet another aspect of the invention provides a method of improving the stool pattern of a formula-fed infant and a method for reducing the incidence of constipation associated with ingestion of infant formula comprising feeding the infant a formula comprising a fat blend as described above. More specifically, the inventive method comprises feeding an infant a nutritionally complete formula comprising a weight ratio of lauric acid to palmitic acid to oleic acid that ranges from 4:3:8 to 1:0.5:3 with a preferred ratio at 2:1:6.

Even more specifically, this invention relates to an infant formula which comprises a source of amino nitrogen, carbohydrates and fat, the improvement characterized in a fat composition comprising 10.4–15.4 weight % lauric acid, 7.5–8.0 weight % palmitic acid and 37.6–43.0 weight % oleic acid and wherein the fat composition is derived from a mixture of oils selected from the group consisting of high oleic safflower oil, high oleic sunflower, soy, coconut, safflower and palm kernel oil.

Further, this invention discloses a method of improving the stool pattern of a formula-fed infant comprising feeding the infant a nutritionally complete composition containing fatty acids, which, based upon the total weight of fatty acid content comprises 10.4–15.0% lauric acid, 7.5–8.0% palmitic acid and 37.6–43.0% oleic acid and wherein the fatty acids are derived from a mixture of high oleic safflower oil, soy oil and coconut oil.

DETAILED DESCRIPTION OF THE PREFERRED EMBODIMENTS

The term "fatty acid profile" as used herein means the total fatty acid content of the fat, oil, emulsifiers and other components used to create an enteral nutritional as determined by convention analysis. Unless specified otherwise, all percentages are weight percents of total fatty acid content. Those skilled in the art will appreciate that sometimes the levels of fatty acids are reported as grams of fatty acid per 100 grams of fat.

In one embodiment, the invention relates to an enteral formula, said formula comprising: 1) protein, said protein being of a concentration of between 10 and 35 grams per liter of formula; 2) carbohydrates, said carbohydrates being of a concentration of between 70 and 110 grams per liter of formula; and 3) fat, said fat having a fatty acid profile comprising 9.5–21 weight percent lauric acid, up to 10 weight % palmitic acid and 34–48 weight % oleic acid. The enteral formula according to this invention provides a source of carbohydrates selected from sucrose, corn syrup, glucose polymers and other carbohydrate sources. The formula may also contain dietary fiber. The teachings of U.S. Pat. No. 5,021,245 are incorporated herein by reference.

(a) In another embodiment, the fat blend further comprises 2.7–3.1 weight % stearic acid, 17–29 weight % linoleic acid and 1.7–3.2 weight % linolenic acid. The fat blend having the recited fatty acid profile can be achieved through a blend of high oleic safflower oil, soy oil and coconut oil. In general, any appropriate source of fatty acids, such as oils, fats, phospholipids, emulsifiers, tissue extracts, single cell oils, recombinant plants, transgenic plants and animals and animals and the like, can be used in this invention, provided less than 10% by weight of total fatty acids is palmitic acid. In an additional embodiment of this invention the weight ratio of linoleic acid to palmitic acid always exceeds 2:1. A further aspect of the invention resides in the discovery of a fatty acid profile for an enteral formula that possesses up to 10 weight % palmitic acid and a weight ratio of lauric acid to palmitic acid to oleic acid of from 3:1:7 to 1.2:1:4.3. The most preferred ratio is about 1.8:1:5.2.

An enteral formula in accordance with the invention may also comprise a nutritionally adequate source of amino nitrogen, carbohydrates, fats, minerals and vitamins, wherein the fat composition consists essentially of 35–55% by weight high oleic safflower oil; 20–40% by weight soy oil; and 20–45% by weight of coconut oil.

The enteral formulas of the invention may be in the form of a ready-to-feed product, a powder or a concentrate. Dilution or reconstitution instructions supplied by the manufacturer should be followed. Those skilled in the art can determine from the instruction conversion factors that would convert the values of such as 10–35 grams per liter of formula for the ready-to-feed product to values applicable to the powdered and concentrate forms.

As used herein, the term "high oleic safflower oil" (HOSO) means the oil derived from the seeds of a hybrid safflower plant, *Carthamus tinctorius*. Safflower oil is an edible oil which typically has a high content of linoleic acid. Hybrids of this plant have been developed which produce a seed oil which has an elevated level of oleic acid. It is the oil that is derived from the seeds of these hybrids which have been found useful in the present invention. Virtually interchangeable with HOSO is high oleic sunflower oil. Like HOSO, high oleic sunflower oil contains an elevated level of oleic acid. When used herein, the term "HOSO" includes its sunflower relative.

As used herein, the term "soy oil" (SO) means the fat fraction obtained from the seeds of the legume, *Soja max*. Typically, the oil fraction of the soya seed undergoes a number of refining, bleaching and deodorization steps resulting in the commercial commodity. Soy oil generally contains relatively high levels of linoleic fatty acid and to a lesser extent, linolenic fatty acid.

As used herein, the term "coconut oil" (CO) means the oil obtained from copra, which is dried coconut meat. This oil is distinguished from HOSO and SO by its high content of saturated, short-chain and medium chain fatty acids. Palm kernel oil is very similar in fatty acid profile to CO. When used herein, the term "CO" includes its palm kernel relative.

As used herein, the terms "stool pattern" and "constipation" relate to kinds of defecation that an individual experiences as a result of nutritional intake. To "improve the stool pattern of a formula-fed infant" means to reduce the actual or perceived difference between the feces consistency of breast-fed infants and those fed a conventional infant formula. As reported above, the consumption of typical infant formula results in infant stools that are firmer/harder than the stools resulting from the consumption of human milk. Human milk is considered the "gold standard" by parents and professional care givers alike. As set forth in Table IV below, infants fed breast milk have stools that can be described as between watery (rank of 1) and slightly above loose/mushy (rank of 2). In the five point scale used to evaluate stool consistency whereby; watery=1, loose/mushy=2, soft=3, formed=4 and hard=5, a difference of 0.3 to 0.4 accompanied by a shift in stool category (i.e., soft to formed) is considered significant. Constipation in adults is considered as a difficult, incomplete, or infrequent evacuation of the bowels. In infants, the term is similar to adults, but uses the breast-fed infant for comparison. Further, this condition is a matter of an actual or perceived condition by the parent or care giver. The breast-fed infant typically has a higher number of stools per day (from about 2.5 to 3.5 per day) and has stools of a looser or watery consistency compared to formula-fed infants. Thus, for both terms, "improving the stool pattern" and "reducing the incidence of constipation", means defecation consistency that more closely resembles the breast-fed infant and a stool of a looser consistency.

The formulas of the invention may take the form of a powdered product, a concentrate or a ready-to feed product. Those skilled in the art will readily appreciate what each form of the product will consist of. In similar fashion, the skilled artisan will understand that reconstitution of the powder and concentrate should follow the instructions of the product manufacturer. As contemplated herein, reconstitution should be accomplished with water and not milk, fruit juices or other liquids that contain protein, carbohydrates or fats.

One aspect of this invention resides in the discovery that particular blends of commodity oils result in a fat composition that possesses a special mixture of fatty acids. The fatty acid profile (predominant) of the commodity oils: soy, coconut, safflower, high oleic safflower, high oleic sunflower, palm kernel and palm olein, are set forth in the following Chart I in an effort to further define and characterize these oils.

Chart I
Fatty Acid Profile of Commodity Oils

| Fatty Acid weight % | Soy | Coconut | Safflower | HOSO | High Oleic Sunflower | Palm Kernel | Palm Olein |
|---|---|---|---|---|---|---|---|
| 12:0 lauric | — | 47.1 | — | 0.1 | — | 49.6 | 0.6 |
| 14:0 myristic | 0.1 | 18.5 | 0.1 | 0.1 | — | 16 | 1.1 |
| 16:0 palmitic | 10.6 | 9.1 | 6.5 | 4.7 | 4.0 | 8.0 | 32.7 |
| 18:0 stearic | 4.0 | 2.8 | 2.4 | 2.2 | 4.0 | 2.4 | 3.5 |
| 18:1n9 oleic | 23.2 | 6.8 | 13.1 | 74.5 | 80.0 | 13.7 | 48.1 |
| 18:2n6 linoleic | 53.7 | 1.9 | 77.7 | 16.7 | 10.0 | 2.0 | 13.2 |
| 18:3n3 linolenic | 7.6 | 0.1 | — | 0.4 | 0.1 | — | 0.5 |

The fatty acid profile of this invention is compared to Enfamil® with Iron, (manufactured by the Mead Johnson Division of Bristol-Meyers, New York, New York); Similac® with Iron (manufactured by the Ross Products Division of Abbott Laboratories, Abbott Park, Ill.) and human milk in the following Chart II:

CHART II
Fatty Acid Profiles of Infant Formulas, the Invention and Human Milk

| Fatty Acid weight % | Enfamil* | Similac* | Invention | Human Milk* |
|---|---|---|---|---|
| 12:0 lauric | 8.4 | 18.0 | 9.5–21 | 1.4–6.5 |
| 14:0 myristic | 3.9 | 7.3 | 3.8–8.4 | 3.8–10.2 |
| 16:0 palmitic | 22.1 | 9.5 | up to 10 | 19.8–24.0 |
| 18:0 stearic | 4.7 | 3.5 | 2.7–3.1 | 7.1–9.0 |
| 18:1n9 oleic | 36.7 | 16.7 | 34–48 | 30.7–38.0 |
| 18:2n6 linoleic | 18.1 | 32.9 | 17–29 | 5.7–17.0 |
| 18:3n3 linolenic | 1.7 | 4.0 | 1.7–3.2 | 0.1–1.8 |

*analyzed

The following Chart III sets forth the fatty acid profile of various embodiments of the present invention.

CHART III

| Fatty Acid weight % | Preferred | More Preferred | Most Preferred |
|---|---|---|---|
| 12:0 lauric | 10.4–17.0 | 10.4–15.0 | 14.2 |
| 14:0 myristic | 4.2–6.7 | 4.2–6.0 | 5.6 |
| 16:0 palmitic | 7.0–8.0 | 7.5–8.0 | 7.7 |
| 18:0 stearic | 2.8–3.1 | 2.9–3.1 | 2.9 |
| 18:1n9 oleic | 37.0–45.2 | 37.6–43.0 | 40.0 |
| 18:2n6 linoleic | 21.0–28.2 | 22.0–28.0 | 22.6 |
| 18:3n3 linolenic | 2.2–3.2 | 2.3–3.2 | 2.3 |

The preferred fatty acid profile as set out above can be accomplished through a blend of 38–50 weight % HOSO, 26–40 weight % SO and 22–36 weight % CO. The more preferred fatty acid profile can be accomplished through a blend of 41–44 weight % HOSO, 27–32 weight % SO, and 27–32 weight % CO. The most preferred fatty acid profile can be accomplished through a blend of 42 weight % HOSO, 28 weight % SO and 30 weight % CO.

Clearly, certain embodiments of the inventive lipid blend are distinguished from commercial fat blends and human milk in the content of lauric, linoleic and palmitic fatty acids. The inventive lipid blend is also distinguished from the prior art formula in the weight ratio of oleic to palmitic fatty acids.

One aspect of the present invention resides in the discovery that an infant formula, to attain stool patterns closer to breast-fed infants, should contain a fat component that is less than 10% by weight palmitic acid. An additional aspect of the inventive oil blend is that the weight ratio of linoleic acid to palmitic acid should always exceed 2:1. In an additional refinement, the weight ratio of oleic to palmitic should always exceed 4:1. A further aspect of the invention resides in the discovery that the fatty acid profile of an infant formula should have a weight ratio of lauric acid to palmitic acid to oleic acid of from 3:1:7 to 1.2:1:4.3. A more preferred ratio is about 1.8:1:5.2.

This invention also relates to a method of reducing the incidence of constipation associated with ingestion of infant formula, said method comprising feeding an infant a nutritionally complete formula comprising: 1) protein; 2) fat, said fat being of a concentration of between 20 and 45 grams per liter of formula; and wherein said fat has a fatty acid profile having a weight ratio of lauric acid to palmitic acid to oleic acid of from 4:3:8 to 1:0.5:3. In amore preferred embodiment the weight ratio is 2:1:6.

From another perspective, the present invention reduces the incidence of constipation through the enteral administration of a fat blend wherein the fat comprises a fatty acid profile with less than 10% by weight of palmitic acid. More specifically, there is disclosed is a method of improving the stool pattern of a formula-fed infant, comprising feeding to the infant a formula comprising high oleic safflower oil, soy oil and coconut oil.

An antioxidant system can be used in conjunction with the invention which consists of β-carotene, R,R,R, α-tocopherol and selenium. The level of R,R,R, α-tocopherol can range from 10 to 30 IU per liter of formula. The level of β-carotene can range from 375 to 575 μg per liter of infant formula and the level of selenium can range from 14 to 32 mcg per liter of formula. The selenium used in this aspect of the invention may be delivered in the form of selenate. The teachings of U.S. Pat. No. 5,221,545 are herein incorporated by reference.

In actual use, the formula of this invention may be consumed by any human. More specifically, the novel fat composition of this invention may be incorporated into a formula which is in compliance with accepted levels of vitamins, minerals, micro-components and the like. The amount consumed does not differ from that associated with the normal consumption of commercially available infant formula. The caloric density (i.e., kcals/ml) and caloric distribution (i.e., the relative proportion of calories from fat, protein and carbohydrate) are not critical to this invention but are generally comparable to conventional formulas. As is well know to those skilled in the art, these factors can vary with the intended use of the formula. For example, pre-term, term and toddler infants have somewhat differing caloric density requirements. Also, formulas for specific disease states (e.g., diabetes, pulmonary deficiency and immunocomprised) will have differing caloric distributions. Those skilled in the art are aware of these differences and will readily adapt the present invention to meet those special needs.

A representative formula for the enteral nutritional product of the invention is set forth in Table I.

TABLE I

A Representative Formula According To The Invention

| NUTRIENT | CONCENTRATION |
| --- | --- |
| Protein | 13.0–20 g/L |
| Protein Source | |
| CSM[1] | 55–75%* |
|  | 7.15–15 g/L |
| WPC[2] | 25–45% |
|  | 3.25–9.0 g/L |

TABLE I-continued

A Representative Formula According To The Invention

| NUTRIENT | CONCENTRATION |
| --- | --- |
| Lipid | 30–40 g/L |
| HOSO | 35–55%** |
| SO | 20–40% |
| CO | 20–45% |
| Carbohydrate | 70–110 g/L |
| Lactose | |

*% by weight of total protein
**% of weight of total lipid
[1]condensed skim milk
[2]whey protein concentrate The pediatric nutritional formula of this invention is generally prepared using the following method. An appropriate quantity of protein is dispersed in sufficient water or oil to solubilize or suspend it, thereby forming a protein solution/suspension. Typically this protein source would be intact milk proteins and/or hydrolyzed milk proteins. In general, any known source of amino nitrogen can be used in this invention. Representative sources of amino nitrogen include bovine milk proteins, vegetable proteins, free amino acids, recombinant proteins, hydrolyzed proteins and mixtures thereof. A carbohydrate source such as one or more of corn syrup solids, lactose, maltodextrins and sucrose is dissolved in water, thereby forming a carbohydrate solution. A source of dietary fiber, such as soy polysaccharide may also be added. Appropriate minerals are dissolved in water, the carbohydrate solution or oil, so as to form a mineral solution.

Once formed, the three solutions (protein, carbohydrate and mineral) are combined in appropriate quantities with oils and oil soluble vitamins. As used herein, the terms "oils", "fats", "phospholipids", "lipids", "lard", and "extracts" means a source of fatty acids that may be provided in the form of glycerides, phospholipids, free fatty acids, the methyl esters of fatty acids and the like. An additional source of fatty acids is derived from emulsifiers that contain fatty acids. Representative of such emulsifiers are the di-acetyl mono-glyceride esters of tartaric acid. This resulting solution is then heat processed and homogenized. Following processing, water soluble vitamins, iron, choline and other nutrients are added and then nucleotides may be added. The solution is then diluted with water to the appropriate caloric density, approximately 670–725 kcal per liter for term infant formula. The formula is then dispensed into containers and retorted to obtain commercial sterility or packaged aseptically using commercially available techniques and equipment. As prepared, the formula contains appropriate nutrients in compliance with the Infant Formula Act as of the date of this application. It should also be recognized that the formula of this invention can be prepared for use in powdered form or as a concentrated liquid.

The invention will be better understood in view of the following examples, which are illustrative only and should not be construed as limiting the invention.

EXAMPLE I

Preparation of Enteral Formula

The following is a representative preparation of an enteral nutritional formula containing the inventive lipid blend. On a commercial scale, two formulas according to the invention were prepared having the compositions set forth in Table II.

The two formula are as close as possible to being identical except for the nucleotide component. These two formulas were then clinically evaluated against human milk for a variety of parameters, including infant stool patterns.

TABLE II

Composition Of Study Feedings (Per Liter)

| NUTRIENT | CONTROL | NUC |
| --- | --- | --- |
| Protein, g | 14.0 | 14.4 |
| Fat, g | 36.5 | 38.3 |
| Carbohydrate, g | 77.1 | 75.5 |
| Calcium, mg | 544.4 | 532.5 |
| Phosphorous, mg | 295.0 | 316.2 |
| Magnesium, mg | 73.5 | 77.7 |
| Sodium, mg | 170.1 | 179.2 |
| Potassium, mg | 931 | 948.6 |
| Chloride, mg | 487.7 | 493.2 |
| Iron, mg | 14.0 | 14.0 |
| Zinc, mg | 5.1 | 5.1 |
| Copper, mcg | 608 | 608 |
| Iodine, mcg | 61 | 61 |
| Manganese, mcg | 34 | 34 |
| Vitamin A, IU | 2930 | 2970 |
| Vitamin D, IU | 405 | 405 |
| Vitamin E, IU | 24.6 | 24.8 |
| Vitamin K, mcg | 54 | 54 |
| Vitamin C, mg | 170 | 172 |
| β-Carotene, mcg | 450 | 450 |
| Selenium, mcg | 23 | 23 |
| Thiamin, mcg | 1350 | 1360 |
| Riboflavin, mcg | 1014 | 1014 |
| Pyridoxine, mcg | 480 | 480 |
| Vitamin $B_{12}$, mcg | 1.7 | 1.7 |
| Niacin, mcg | 7095 | 7095 |
| Folic Acid, mcg | 101 | 101 |
| Pantothenic acid, mcg | 3041 | 3041 |
| Biotin, mcg | 30 | 30 |
| Taurine, mg | 45 | 45 |
| Choline, mg | 108 | 108 |
| Inositol, mg | 32 | 32 |
| Energy, Kcal | 676 | 676 |
| CMP, mg | 2.72* | 31.2 |
| UMP, mg | 4.19* | 17.7 |
| AMP, mg | 0.57* | 9.8 |
| GMP, mg | 0.45* | 14.4 |

*inherent to the source of protein.

In this Example, a 7711 Kg batch of each formula was prepared. In a similar fashion, the CON formula differed from NUC in that the nucleotides were omitted. The list of ingredients and amounts are found in Table III.

TABLE III

Ingredients And Amounts For NUC Formula

| INGREDIENT | AMOUNT |
| --- | --- |
| High Oleic Safflower Oil | 120.2 Kg |
| Coconut Oil | 85.7 Kg |
| Soy Oil | 80.3 Kg |
| Lecithin | 2.92 Kg |
| Mono-and diglyceride | 2.92 Kg |
| Oil Soluble Vit, Premix | 0.365 Kg |
| β-carotene | 0.0137 Kg |
| Carrageenan | 1.43 Kg |
| Whey Protein Concentrate | 61.2 Kg |
| Lactose | 476.3 Kg |
| Potassium Citrate | 4.6 Kg |
| Magnesium Chloride | 0.735 Kg |
| Low Heat Condensed Skim Milk | 821 Kg |
| Calcium Carbonate | 3.36 Kg |
| Ferrous sulfate | 0.450 Kg |
| Water Soluble Vitamin Premix Trace Minerals/Taurine | 1.11 Kg |

TABLE III-continued

Ingredients And Amounts For NUC Formula

| INGREDIENT | AMOUNT |
| --- | --- |
| Choline Chloride | 0.600 Kg |
| Adenosine 5'monophosphate | 0.113 Kg |
| Guanosine 5'monophosphate-Na2 | 0.197 Kg |
| Cytidine 5'monophosphate | 0.259 Kg |
| Uridine 5'monophosphate-Na2 | 0.216 Kg |
| Ascorbic Acid | 1.78 Kg |
| 45% KOH | 2.36 Kg |
| Total Yield | 7711 Kg |

The first step in the preparation of formulas is the preparation of the oil blend. To an appropriately sized blend tank with agitation and heating soy oil, coconut oil and high oleic safflower oil were added. The mixture was heated to 73.8–79.4° C. The lecithin and mono-and diglycerides (Myverol 18-06) were added to the blend tank with agitation. The oil soluble vitamin premix was added with agitation. The premix container was rinsed with the oil blend and transferred back to the blend tank to ensure complete delivery of the vitamin premix. The β-carotene was added to the oil blend and the mixture agitated until the components were well dispersed. The β-carotene container was rinsed with the oil blend and the contents returned to the blend tank to ensure complete delivery of the β-carotene solution. Lastly, the carrageenan was added to the oil blend and the mixture was agitated and held at 54.0–60° C. until used.

The carbohydrate, mineral and CSM (condensed skim milk) protein slurry was prepared next. To water heated to 68–73° C. the lactose was added and the mixture agitated until the lactose was well dissolved. Potassium citrate was then added followed by potassium chloride, sodium chloride and magnesium chloride. The condensed skim milk (CSM) and tri-calcium phosphate were then added and the mixture was agitated and held at 54–60° C. until used.

The protein-in-water (PIW) slurry was then prepared. The whey protein concentrate was added to water at 54–60° C. under mild agitation. The PIW slurry was held under mild agitation until needed. Also contemplated in this invention is the use of protein-in-fat (PIF) slurries, wherein an appropriate amount of protein is admixed with all or a portion of the oil (fat) component.

The PIW slurry was then added to the prepared oil blend. The required amount of the carbohydrate, mineral and CSM slurry was then added to the oil blend. The pH of the mixture was then determined and if below specification, it was adjusted using KOH to a pH of 6.75 to 6.85. The mixture was then held at 54–60° C. under agitation for at least 15 minutes.

The mixture was then heated to 68–74° C. and deaerated under vacuum. The mixture was then emulsified through a single stage homogenizer at 6.21 to 7.58 MPa. After emulsification, the mixture was heated to 120–122° C. for 10 seconds and then 149–150° C. for 5 seconds. The mixture was then passed through a flash cooler to reduce the temperature to 120–122° C. and then through a plate cooler to reduce the temperature to 71–79° C. The mixture was then passed through a two stage homogenizer at 26.89 to 28.27 MPa and 2.76 to 4.14 MPa. The mixture was held at 73 to 83° C. for 16 seconds and then cooled to 1 to 7° C. At this point, samples are taken for microbiological and analytical testing. The mixture was held under agitation.

A calcium carbonate solution may be prepared for use in adjusting the calcium level of the mixture if outside of specification.

A vitamin stock solution was prepared. To water heated at 37 to 66° C. was added potassium citrate and ferrous sulfate. The vitamin premix was then added and the mixture agitated. The choline chloride was added and then the required amount of this vitamin mixture was added to the batch.

The nucleotide solution was then prepared. The following nucleotides were added to water with mild agitation in the following order: AMP, GMP, CMP, UMP. Agitation was continued for about 10 minutes to dissolve the nucleotides. The nucleotide solution was then added to the batch.

Lastly, an ascorbic acid solution was prepared and added slowly to the batch with agitation for at least 10 minutes. Final dilution with water to meet specified levels of solids and caloric density was completed. The batch was then packaged in 0.9 Kg (32 ounce) metal cans and sterilized using conventional technology.

EXAMPLE II

Clinical Study of Enteral Formula

The initial purpose of this clinical investigation was to determine the effect of a nucleotide-fortified formula according to the present invention on the development of the neonatal immune system as measured by the antibody response to childhood vaccines. This clinical investigation, also demonstrates that the inventive oil blend (HOSO, SO and CO) provided an infant stool pattern that closely resembles the breast-fed infant.

This was a 12-month, randomized, controlled, blinded, multi-site trial of term infants. Infants enrolled into the study received human milk (HM) or one of two clinically labeled formulas: 1) control formula (CON); or 2) CON formula supplemented with nucleotides (NUC). The analyzed composition of each formula is set forth in Table II. A total of 311 infants completed the study (107 CON, 101 NUC and 103 HM). Infants followed the immunization schedule recommended by the American Academy of Pediatrics with single lots of Hib TITER® Hemophilus influenzae type B conjugate vaccine (Diphtheria CRM 197 and tetanus protein conjugate sold by Lederle, Inc.) and Diphtheria and Tetanus Toxoids and Pertussis Vaccine Adsorbed, sold by Lederle, Inc. Infants were full term with a gestations age of 38–42 weeks, at or above the $5^{th}$ percentile for weight, length and head circumference and were enrolled between 2 and 10 days of age. All subjects were healthy with no indication of systemic disease and did not receive any medications, mineral or vitamin supplements.

The primary outcome variable investigated was vaccine response at 6, 7 and 12 months of age. Outcome variables also included intake, anthropometry, and indicia of tolerance (stool characteristics and incidence of spit-up).

Experimental Design

At 2, 4 and 6 months of age, DPT and Hib vaccines were administered. Parents of the infants agreed to feed the infant only study formula until 4 to 6 months of age when table foods were added to supplement the study formula. The HM fed group were exclusively breast fed up to 2 months of age and a mixture of HM and Similac® with Iron (Ross Products Division of Abbott Laboratories) after 2 months, if necessary.

Weight, length and head circumferences were measured at 21 days of age and at 2, 4, 5, 6 and 12 months of age. Three-day records of formula intake, frequency of spit-up and vomiting and the frequency, color and consistency of stools were used to assess tolerance.

Statistical Methods

Anthropometric data were analyzed for each gender separately. Analysis of Variance (ANOVA) was done at birth, initial visit, 2, 4, 6, 7 and 12 months of age for weight, length and head circumference. Stool variables were ranked and analyzed with ANOVAs (number of stools, mean rank consistency and percent of stools with gas or unusual odor).

Results

Substantial amounts of data were collected on each of the 311 infants enrolled in this clinical investigation. Below is a summary of the information that supports the novel and unobvious features of the instant invention.

Growth of infants was similar in all three groups. Tolerance and intake was similar for the two formula groups. The similarity in growth and tolerance among all infants demonstrated that both formulas are acceptable, however, for the first time, a stool pattern similar to HM was found.

The anthropometric measurements indicate that growth was comparable among all infants in the study. The fact that even before controlling for birth values there were no differences among males for weight, length or head circumference gives assurance that growth was acceptable among all groups.

The higher stool frequency and number of feedings per day of HM-fed infants compared to formula-fed infants during the first 2 months is well established. Softer stools of HM-fed infants are also common. However in this study, the difference observed was in the NUC group at 2 months and was only a small amount. Overall, the measures of tolerance among all groups were very similar through 4 months when half the infants were still being exclusively breast-fed. These data demonstrate both formulas were extremely well tolerated and are set forth in Table IV. These data also suggest that the inventive lipid blend produced infant stool patterns very similar to infants consuming breast milk. This is a surprising observation as stool patterns of prior art infant formula were always harder than the stools of infants fed breast milk.

TABLE IV

INTAKE AND TOLERANCE MEAN (SEM)[1]

| | 2 MONTHS | | |
|---|---|---|---|
| | NUC 100 | CON 107 | HM 103 |
| Feedings (#/day) | 6.2 (0.1) | 6.2 (0.1) | 7.7 (0.2) |
| Intake (mL/day) | 831 (19) | 823 (18) | ND |
| Spit-up (% of feedings) | 8 (2) | 18 (2) | 20 (2) |
| Stool Frequency (#/day) | 1.6 (0.1) | 1.4 (0.1) | 2.7 (0.2) |
| Stool Consistency[2] | 2.0 (0.1) | 1.9 (0.1) | 1.7 (0.1) |

| | 4 MONTHS | | |
|---|---|---|---|
| | NUC 98 | CON 107 | HM 103 |
| Feedings (#/day) | 5.9 (0.1) | 6.0 (0.1) | 6.6 (0.2) |
| Intake (mL/day) | 987 (33) | 926 (17) | ND |
| Spit-up (% of feedings) | 22 (2) | 18 (2) | 20 (2) |
| Stool Frequency (#/day) | 1.4 (0.1) | 1.4 (0.1) | 1.5 (0.1) |
| Stool Consistency[2] | 2.0 (0.1) | 2.1 (0.1) | 2.1 (0.1) |

[1]- Values in the same row with different superscripts are significantly different: $P < 0.05$
[2]- Mean rank consistency, where 1 = water, 2 = mushy, 3 = soft, 4 = formed, 5 = hard These data also support an additional aspect of the instant invention—lipid sources which are less than 10% by weight palmitic fatty acid will provide stool patterns that are similar to breast-fed infants.

EXAMPLE III

In this experiment an investigation of protein sources and lipid sources were evaluated. A randomized and blinded tolerance study was conducted. Two levels of each factor were studied: Protein: 100% nonfat milk (CSM) or 64% by weight nonfat milk plus 36% whey protein; and Lipid: soy/coconut (conventional infant formula oil blend) or HOSO, SO and CO (inventive oil blend). Infants were fed commercially available Similac® with Iron (Ross Products Division of Abbott Laboratories, Columbus, Ohio) during a 1 week baseline period and then randomized to receive one of eight experimental formulas for an additional two weeks. Those eight experimental formulas consisted of two groups of four formulas which differed in method of manufacture. For purposes of this application, the two groups were combined and thus four formulas are reported herein. Eight (8) sites were used to recruit infants, each having a birth-weight greater than 2.5 Kg. Primary outcome variables were stool frequency, stool consistency and incidence of vomit and spit up.

The analyzed composition of each formula is set forth in Table V. The protein system was either 100% CSM (nonfat milk) or a blend of 64% nonfat milk and 36% whey protein (WP). The lipid blend was either 60/40% by weight soy and coconut oils (SWI, a.k.a. Similac® with Iron) or 42/30/28% high oleic safflower, coconut and soy oils (ALT, a.k.a. Alternative Lipid Test). Similac® with Iron, manufactured by the Ross Products Division of Abbott Laboratories, Columbus, Ohio, was used as a baseline nutritional. Formulas were packaged in clinically labeled 0.9 Kg (32 ounce) cans and provided 67.7 kcal/100 ml (20 kcal/fl.oz). All formulas met or exceeded levels of nutrients as recommended by the Committee on Nutrition of the American Academy of Pediatrics and the Infant Formula Act, 1980.

Parents were instructed to begin feeding their infants the baseline formula immediately after enrollment and were given forms to record the volume of each feeding, incidences of spit up and vomiting, and stool characteristics during Days 2–7. At the Day 8 visit to the pediatrician's office, parents returned any unused formula and were given the assigned study formula. Dietary/stool records were again completed daily during study days 9–21.

The analyses of variables were done to evaluate all main effects and interactions. This study evaluated a number of variables of which, only a few are presented herein. For each variable, the effects of interest were tested using analysis of covariates (ANCOVA) with baseline values as covariates. An intent-to-treat analysis was carried out. All results were considered statistically significant at the 0.05 level. Multiple comparisons for significant effects in the ANCOVA models were carried out by comparing least-squares means. A Bonferroni-type adjustment was made to the individual P-values to ensure an overall level of 0.05 for all comparisons.

TABLE VI

MEAN RANK STOOL CONSISTENCY*

| Factor | Study Period |
|---|---|
| Protein | |
| WP Mean | 2.1 |
| CSM Mean | 2.2 |
| Lipid | |
| ALT Mean[a] | 2.0 |
| SWI Mean[b] | 2.4 |

TABLE V

ANALYZED COMPOSITION OF STUDY FORMULAS (PER LITER)*

| NUTRIENT | CSM/SWI | CSM/ALT | WP/SWI | WP/ALT | Similac ® Baseline Feed |
|---|---|---|---|---|---|
| Protein, g | 14.8 | 14.1 | 14.2 | 13.2 | 14.8 |
| Source | nonfat milk | nonfat milk | whey, nonfat milk | whey, nonfat milk | nonfat milk |
| Fat, g | 36.9 | 34.7 | 36.3 | 34.5 | 37.3 |
| Source | SWI | ALT | soy and coconut oils | HOSO, soy and coconut oils | soy and coconut oils |
| Carbohydrate, g | 79.3 | 74.6 | 73.6 | 70.3 | 73.3 |
| Source | lactose | lactose | lactose | lactose | lactose |
| Minerals | | | | | |
| Calcium, mg | 560 | 525 | 537 | 514 | 544 |
| Phosphorous, mg | 463 | 334 | 333 | 321 | 476 |
| Magnesium, mg | 64.3 | 55.1 | 56.2 | 53.7 | 62.6 |
| Sodium, mg | 210 | 176 | 174 | 171 | 187 |
| Potassium, mg | 821 | 1010 | 952 | 949 | 837 |
| Chloride, mg | 510 | 493 | 519 | 488 | 512 |
| Iron, mg | 13.4 | 14.0 | 13.8 | 13.7 | 12.7 |
| Vitamins | | | | | |
| A, IU | 3161 | 3008 | 3081 | 2860 | 3194 |
| E, IU | 24.2 | 23.1 | 23.6 | 22.1 | 22.3 |
| C, mg | 120 | 164 | 91 | 144 | 269 |
| Thiamine ($B_1$), mg | 1.48 | 1.41 | 1.43 | | |
| Pyridoxine ($B_6$), mg | 0.48 | 0.50 | 0.48 | 0.48 | 0.48 |

:- based on compendium value for ash
*- 8 batches were prepared, however, the batches of differing manufacturing methods were combined for this study.

TABLE VI-continued

MEAN RANK STOOL CONSISTENCY*

| Factor | Study Period |
|---|---|

*= Values with unlike superscripts are significantly different at P < 0.05 with a < b. Protein: WP = whey and nonfat milk, CSM = nonfat milk; Fat: SWI = soy and coconut oils, ALT = high oleic safflower, soy and coconut oils.

Stool Consistency

Mean Rank Stool Consistency, as set forth in Table VI, clearly demonstrates that the lipid blend of this invention produces a softening of infant stools. It was further determined that type of protein had no measurable impact on stool consistency.

A significant effect of lipid was observed for predominant stool consistency. The data is reported in Table VII. The SWI lipid blend was associated with firmer stools. The percentage of stools of each consistency is shown in Table VII. An effect of lipid was found in the watery, soft and formed categories of stool consistencies with the SWI oil blend producing an overall firmer stool.

TABLE VII

Distribution of Predominant Stool Consistency[†]

| | STUDY PERIOD | | | | |
|---|---|---|---|---|---|
| Factor | W | L/M | S | F | H |
| PROTEIN | | | | | |
| WP Mean | 26 | 42 | 26 | 4 | 1 |
| CSM Mean | 25 | 39 | 27 | 7 | 3 |
| LIPID | | | | | |
| ALT Mean | 37[a] | 37 | 20[b] | 4[b] | 2 |
| SWI Mean | 15[b] | 44 | 33[a] | 7[a] | 1 |

[†]Values are average daily % of stools. Values with unlike superscripts are significantly different at P < 0.05 with a > b. W = watery, L/M = loose/mushy, S = soft, F = formed, H = hard. Protein: WP = whey and nonfat milk, CSM = nonfat milk; Fat: SWI = soy and coconut oils, ALT = high oleic safflower, soy and coconut oils.

The main effect of the lipid component was on stool consistency. This was due to a greater percentage of infants experiencing a softer stool consistency with ALT. The results indicate that ALT oil contributes to softer infant stools. The data supports the conclusion that the ALT oil blend is associated with softer, more watery stools.

EXAMPLE IV

Powdered Formula

In this experiment, powdered formulas having different oil blends and protein sources were evaluated for their ability to soften infant stools. As a result of the knowledge obtained from Example IV, it was concluded that protein, as used in Example III and this experiment, has no appreciable effect on stool consistency. The Control formula was powdered Similac® with Iron. The Experimental formula used a 64/36 weight % nonfat milk/whey protein base and the inventive 42/28/30 weight % HOSO/SO/CO blend.

A clinical study similar to those previously described, was initiated. The two week study was completed by 30 Control-fed infants and 27 Experimental-fed infants. After the initial baseline feeding, stool data was collected from day 22 through day 34. The results of the study are set forth in Table VIII.

TABLE VIII

Stool Characteristics

| PARAMETER | CON | EXP |
|---|---|---|
| Mean Rank Stool* Consistency | 3.1[a] | 2.1[b] |
| Average Daily %** | | |
| Watery | 3.7[b] | 24.2[a] |
| Loose/Mushy | 25.2[c] | 45.9[d] |
| Soft | 40[d] | 19.4[c] |
| Formed | 20.2[b] | 8.4[a] |
| Hard | 10.9[b] | 2.0[a] |

*Stool consistency ranked as watery = 1, loose/mushy = 2, soft = 3, formed = 4, and hard = 5; categories were defined as Watery - loose and runny; Loose/Mushy - spread over diaper, covered with mucous; Soft - spread over diaper, pasty; Formed - has some shape in diaper, yet moist; and Hard - well shaped and appears to contain little water.
**Calculated as % of individual's stools, followed by deriving a mean value for all infants.
[a,b]Values in same row are significantly different, P < 0.01.
[c,d]Values in same row are significantly different, P < 0.05.

The data when analyzed as a percent of infants that reported a predominance of stools in a given category is presented in Table IX.

TABLE IX

Predominant Stool Consistencies % of Infants

| PARAMETER | CON | EXP |
|---|---|---|
| Watery | 0 | 23 |
| Loose/Mushy | 21 | 46 |
| Soft | 46 | 27 |
| Formed | 21 | 4 |
| Hard | 11 | 0 |

Table VIII and IX clearly demonstrates that a significant difference in distribution of stool patterns is achieved with the inventive oil blend.

These recent, extensive clinical studies support the results originally reported in the parent patent application—the oil blend of this invention provides a stool pattern that closely resembles the stool pattern of breast-fed infants. Further, the use of the novel oil blend of this invention addresses the reported concerns association with conventional infant formula.

Numerous additional studies have been conducted which are only redundant to the work reported herein. This extensive and costly research has advanced the state of the art of human nutrition and forms the basis of the claims presented in this application.

Industrial Applicability

The results from these experiments demonstrate that the enteral formula of this invention is effective in producing stool patterns that are similar to breast-fed infants and that problems typically associated or perceived to be associated with conventional infant formula, especially iron fortified formula, can be alleviated through the use of the novel oil blend of this invention. The medical community is constantly searching for nutritional formulas that will benefit the infant. The present invention can clearly fill that need. The manufacture of the formula utilizes conventional equipment and may be readily accomplished.

While the infant formula and method of making said formula herein described constitute a preferred embodiment of this invention, it is to be understood that the invention is not limited to this precise formulation or method and that changes may be made therein without departing from the scope of the invention which is defined in the appended claims.

We claim:

1. An improved fat composition for consumption by humans, wherein said fat composition comprises, based on the weight of the total fat:
   a) 35–55 weight % high oleic safflower oil;
   b) 20–40 weight % soy oil, and;
   c) 20–45 weight % coconut oil, with the proviso that said fat composition does not contain oleo oil, randomized palm oil or randomized palm olein oil.

2. The fat composition of claim 1 comprising:
   a) 38–50 weight % high oleic safflower oil;
   b) 26–40 weight % soy oil, and;
   c) 22–36 weight % coconut oil.

3. The fat composition according to claim 1 comprising:
   a) about 42 weight % high oleic safflower oil;
   b) about 28 weight % soy oil, and;
   c) about 30 weight % coconut oil.

4. An enteral formula comprising:
   a) a source of amino nitrogen;
   b) a source of carbohydrate, and;
   c) said fat composition according to claim 1.

5. An enteral formula comprising:
   a) a source of amino nitrogen:
   b) a source of carbohydrate, and;
   c) said fat composition according to claim 2.

6. An enteral formula comprising:
   a) a source of amino nitrogen;
   b) a source of carbohydrate, and;
   c) said fat composition according to claim 3.

7. The formula of claim 4 wherein said formula is in the form of a powder intended to be reconstituted, a concentrate intended to be reconstituted or a ready-to-feed liquid.

8. The formula of claim 7 which is in said ready-to-feed form and wherein:
   a) said amino nitrogen source is at a concentration of between 10 and 35 grams per liter of said formula;
   b) said carbohydrates is at a concentration of between 60 and 100 grams per liter of said formula, and;
   c) said fat composition is at a concentration of between 20 and 45 grams per liter of said formula.

9. An enteral formula for infants comprising:
   a) from 13.0–20 grams of a protein source per liter of said formula;
   b) from 13–21 grams of a source of lipid per liter of said formula, in which said lipid further comprises:
      i) from 35–55 weight % high oleic safflower oil,
      ii) from 20–40 weight % soy oil and,
      iii) from 20–45 weight % coconut oil, with the proviso that said lipid does not contain oleo oil, randomized palm oil or randomized palm olein oil. and;
   c) from 70–110 grams of a carbohydrate source per liter.

10. An improved fat composition for consumption by humans, wherein said fat composition consists essentially of, based on the weight of the total fat:
    a) 35–55 weight % high oleic safflower oil;
    b) 20–40 weight % soy oil, and;
    c) 20–45 weight % coconut oil, with the proviso that said fat composition does not contain oleo oil, randomized palm oil or randomized palm olein oil.

11. The fat composition of claim 10 consisting essentially of:
    a) 38–50 weight % high oleic safflower oil;
    b) 26–40 weight % soy oil, and;
    c) 22–36 weight % coconut oil.

12. The fat composition according to claim 10 consisting essentially of:
    a) about 42 weight % high oleic safflower oil;
    b) about 28 weight % soy oil, and;
    c) about 30 weight % coconut oil.

13. An enteral formula comprising:
    a) a source of amino nitrogen;
    b) a source of carbohydrate, and;
    c) said fat composition according to claim 10.

14. The formula of claim 13 wherein said formula is in the form of a powder intended to be reconstituted, a concentrate intended to be reconstituted or a ready-to-feed liquid.

15. The formula of claim 14 which is in said ready-to-feed form and wherein:
    a) said amino nitrogen source is present at a concentration of between 10 and 35 grams per liter of said formula;
    b) said carbohydrate is present at a concentration of between 60 and 100 grams per liter of said formula, and;
    c) said fat composition is present at a concentration of between 20 and 45 grams per liter of said formula.

16. An enteral formula for infants comprising:
    a) from 13.0–20 grams of a protein source per liter of said formula;
    b) from 13–21 grams of a source of lipid per liter of said formula in which said lipid consists essentially of:
       i) from 35–55 weight % high oleic safflower oil,
       ii) from 20–40 weight % soy oil and,
       iii) from 20–45 weight % coconut oil, with the proviso that said fat composition does not contain oleo oil, randomized palm oil or randomized palm olein oil. and;
    c) from 70–110 grams of a carbohydrate source per liter.

* * * * *